United States Patent [19]
Chenard et al.

[11] Patent Number: 6,060,479
[45] Date of Patent: May 9, 2000

[54] QUINAZOLINE-4-ONE AMPA ANTAGONISTS

[75] Inventors: Bertrand L. Chenard, Waterford; Willard M. Welch, Mystic, both of Conn.

[73] Assignee: Pfizer Inc, New York, N.Y.

[21] Appl. No.: 09/079,419

[22] Filed: May 14, 1998

Related U.S. Application Data

[60] Provisional application No. 60/049,083, Jun. 9, 1997.

[51] Int. Cl.[7] ...................... A61K 31/505; C07D 239/72; C07D 495/02; C07D 401/04; C07D 403/00
[52] U.S. Cl. .......................... 514/258; 514/259; 544/278; 544/284; 544/287; 544/290
[58] Field of Search ..................................... 514/258, 259; 544/278, 284, 287, 290

[56] References Cited

U.S. PATENT DOCUMENTS 4,183,931  1/1980  Wolfe et al. ............................. 424/251

OTHER PUBLICATIONS

Watkins, J.C., and Evans, R.H., Excitatory Amino Acid Transmitters, Annu. Rev. Pharmacol. Toxicol. 21, pp. 165–204 (1981).

Monaghan, Daniel T., et al., The Excitatory Amino Acid Receptors: Their Classes, Pharmacology, and Distinct Properties in the Function of the Central Nervous System, Annu. Rev. Pharmacol. Toxicol. 29 pp. 365–402 (1989).

Watkins, Jeff C., et al., Structure–activity relationships in the development of excitatory amino acid receptor agonists and competitive antagonists, TIPS–(vol. 11) pp. 25–33 Jan. 1990.

Schoepp, Darryle, et al., Pharmacological and functional characteristics of metabotropic excitatory amino acid receptors, TIPS–(vol. 11) pp. 508–515 Dec. 1990.

McDonald, John W. and Johnston, Micheal V., Physiological and pathophysiological roles of excitatory amino acids during central nervous system development, Brain Res. Reviews 15, pp. 41–70 (1990).

Sheardown, Malcom J., et al., 2,3–Dihydroxy–6–nitro–7–sulfamoyl–benzo(F) quinoxaline: A Neuroprotectant for Cerebral Ischemia, Science Reports, vol. 247, pp. 571–574 Feb. 2, 1990.

Buchan, Alastair M., et al., Delayed AMPA receptor blockade reduces cerebral infarction induced by focal ischemia, NeuroReport 2, No. 8, pp. 473–476 (1991).

Le Peillet, Elaine, et al., The non–NMDA antagonists, NBQX and GYKI 52466, protect against cortical and striatal cell loss following transient global ischaemia in the rat, Brain Res. 571, pp. 115–120 (1992).

Parks T.N., et al., Modulation of N–methyl–D–aspartate receptor–mediated increases in cytosolic calcium in cultured rat cerebellar granule cells, Brain Res. 552, pp. 13–22 (1991).

Wolfe, James F., et al., Synthesis and Anticonvulsant Activity of Some New 2–Substituted 3–Aryl–4 (3H)–quinazolinones, J. Med. Chem, 33, pp. 161–166, (1990).

Wolfe, James F., et al., Synthesis and Anticonvulsant Activity of Some New 3, 6–Disubstituted–2–[2–oxo–2–(4–pyridyl)ethyl]–4(3H)–pyrimidinones, Journal of Pharmaceutical Sciences, vol. 80, No.7, pp. 705–706 Jul. 1991.

Beal, M. Flint, Aging, Energy, and Oxidative Stress in Neurodegenerative Diseases, Annals of Neurology, vol. 38, No. 3, pp. 357–366, Sep. 1995.

*Primary Examiner*—Richard L. Raymond
*Assistant Examiner*—Brenda Coleman
*Attorney, Agent, or Firm*—Peter C. Richardson; Paul H. Ginsburg

[57] ABSTRACT

The present invention relates to novel quinazolin-4-one derivatives of the formula I, as defined in the specification, pharmaceutical compositions containing such compounds the use of such compounds to treat neurodegenerative, psychotropic, and drug and alcohol induced central and peripheral nervous system disorders.

20 Claims, No Drawings

QUINAZOLINE-4-ONE AMPA ANTAGONISTS

This application claims the benefit of U.S. Provisional Application Ser. No. 60/049,083, filed Jun. 9, 1997.

BACKGROUND OF THE INVENTION

The present invention relates to quinazolin-4-ones of the formula I, as described below, their pharmaceutically acceptable salts, pharmaceutical compositions containing them and their use in treating neurodegenerative, psychotropic, and drug and alcohol induced central and peripheral nervous system disorders.

The role of excitatory amino acids, such as glutamic acid and aspartic acid, as the predominant mediators of excitatory synaptic transmission in the central nervous system has been well established. Watkins & Evans, *Ann. Rev. Pharmacol. Toxicol.*, 21, 165 (1981); Monaghan, Bridges, and Cotman, *Ann. Rev. Pharmacol. Toxicol.*, 29, 365 (1989); Watkins, Krogsgaard-Larsen, and Honore, *Trans. Pharm. Sci.*, 11, 25 (1990). These amino acids function in synaptic transmission primarily through excitatory amino acid receptors. These amino acids also participate in a variety of other physiological processes such as motor control, respiration, cardiovascular regulation, sensory perception, and cognition.

Excitatory amino acid receptors are classified into two general types. Receptors that are directly coupled to the opening of cation channels in the cell membrane of the neurons are termed "ionotropic." This type of receptor has been subdivided into at least three subtypes, which are defined by the depolarizing actions of the selective agonists N-methyl-D-aspartate (NMDA), α-amino-3-hydroxy-5-methylisoxazole-4-propionic acid (AMPA), and kainic acid (KA). The second general type is the G-protein or second messenger-linked "metabotropic" excitatory amino acid receptor. This second type, when activated by the agonists quisqualate, ibotenate, or trans-1-aminocyclopentane-1,3-dicarboxylic acid, leads to enhanced phosphoinositide hydrolysis in the postsynaptic cell. Both types of receptors appear not only to mediate normal synaptic transmission along excitatory pathways, but also participate in the modification of synaptic connection during development and changes in the efficiency of synaptic transmission throughout life. Schoepp, Bockaert, and Sladeczek. *Trends in Pharmacol. Sci.*, 11, 508 (1990); McDonald and Johnson, *Brain Research Reviews*, 15, 41 (1990).

The excessive or inappropriate stimulation of excitatory amino acid receptors leads to neuronal cell damage or loss by way of a mechanism known as excitotoxicity. This process has been suggested to mediate neuronal degeneration in a variety of conditions. The medical consequences of such neuronal degeneration makes the abatement of these degenerative neurological processes an important therapeutic goal.

Excitatory amino acid excitotoxicity has been implicated in the pathophysiology of a number of neurological disorders. This excitotoxicity has been implicated in the pathophysiology of acute and chronic neurodegenerative conditions including stroke, cerebral ischemia, spinal cord trauma, head trauma, Alzheimer's Disease, Huntington's Chorea, amyotrophic lateral sclerosis, epilepsy, AIDS-induced dementia, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, ocular damage and retinopathy, idiopathic and drug-induced Parkinson's Disease and cerebral deficits subsequent to cardiac bypass surgery and grafting. Other neurological conditions that are caused by glutamate dysfunction require neuromodulation. These other neurological conditions include muscular spasms, migraine headaches, urinary incontinence, psychosis, addiction withdrawal (such as alcoholism and drug addiction including opiate, cocaine and nicotine addiction), opiate tolerance, anxiety, emesis, brain edema, chronic and acute pain, convulsions, retinal neuropathy, tinnitus and tardive dyskinesia. The use of a neuroprotective agent, such as an AMPA receptor antagonist, is believed to be useful in treating these disorders and/or reducing the amount of neurological damage associated with these disorders. The excitatory amino acid receptor (EAA) antagonists are also believed to be useful as analgesic agents.

Several studies have shown that AMPA receptor antagonists are neuroprotective in focal and global ischemia models. The competitive AMPA receptor antagonist NBQX (2,3-dihydroxy-6-nitro-7-sulfamoylbenzo[f-]quinoxaline) has been reported effective in preventing global and focal ischemic damage. Sheardown et al., *Science*, 247, 571 (1900); Buchan et al., *Neuroreport*, 2, 473 (1991); LePeillet et al., *Brain Research*, 571, 115 (1992). The noncompetitive AMPA receptor antagonist GKYI 52466 has been shown to be an effective neuroprotective agent in rat global ischemia models. LaPeillet et al., *Brain Research*, 571, 115 (1992). These studies strongly suggest that the delayed neuronal degeneration in brain ischemia involves glutamate excitotoxicity mediated at least in part by AMPA receptor activation. Thus, AMPA receptor antagonists may prove useful as neuroprotective agents and improve the neurological outcome of cerebral ischemia in humans.

SUMMARY OF THE INVENTION

The present invention relates to compounds of the formula

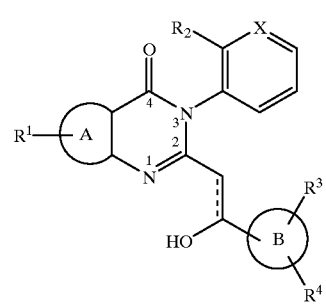

wherein the dashed line represents an optional double bond;

A is a benzo or thieno fused aromatic ring;

B is phenyl, pyridyl or pyrimidyl;

X is N or CH;

$R^1$ is selected from hydrogen, $(C_1-C_6)$alkyl optionally substituted with from one to three fluorine atoms, cyano, halo, amino, nitro and $(C_1-C_6)$alkoxy optionally substituted with from one to three fluorine atoms;

$R^2$ is halo, cyano, $(C_1-C_6)$ alkyl optionally substituted with from one to three fluorine atoms, nitro, amino, $(C_1-C_6)$ alkylthio, $(C_1-C_6)$alkoxy optionally substituted with from one to three fluorine atoms, hydroxy, H—C(=O)—, $(C_1-C_6)$alkyl—O—C(=O)— or $NH_2$—C(=O)—;

$R^3$ and $R^4$ are selected, independently, from hydrogen, $(C_1-C_6)$alkyl optionally substituted with from one to three fluorine atoms, halo, cyano, hydroxy $(C_1-C_6)$alkoxy optionally substituted with from one to three fluorine atoms, —C(=O)H, —CH$_2$OR$^5$ and —CH$_2$NR$^6$R$^7$;

R$^5$ is hydrogen, (C$_1$–C$_6$)alkyl or —C(=O)(C$_1$–C$_6$)alkyl; and

R$^6$ and R$^7$ are selected, independently, from hydrogen, (C$_1$–C$_6$)alkyl, —C(=O)H and —C(=O)(C$_1$–C$_6$)alkyl;

or R$^6$ and R$^7$, taken together with the nitrogen to which they are attached, form a four to seven membered saturated or unsaturated ring wherein one of the carbon atoms of such ring may optionally be replaced by oxygen or nitrogen (for example, a morpholine, piperidine, pyrrolidine, piperizine, azetidine, pyrrole, pyridine or oxazoline ring);

and the pharmaceutically acceptable salts of such compounds.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

Examples of preferred compounds of the formula I are those wherein R$^1$ is fluoro.

Other examples of preferred compounds of the formula I are those wherein ring A is benzo.

Other examples of preferred compounds of the formula I are those wherein ring A is benzo and R$^1$ is fluoro.

Other examples of preferred compounds of the formula I are those wherein ring A is benzo, R$^1$ is fluoro, R$^2$ is chloro and the bond represented by both solid and dashed lines is a carbon-carbon double bond.

Other examples of preferred compounds of the formula I are wherein R$^2$ is halo, methyl or trifluoromethyl.

Other examples of preferred compounds of the formula I are those wherein R$^1$ is fluoro and R$^2$ is chloro.

Other examples of preferred compounds of the formula I are those wherein R$^3$ and R$^4$ are selected, independently from 2-cyano, 3-cyano, 2-formyl, 3-(C$_1$–C$_6$)alkyl, 3-halo, 2-halo and 3-CH$_2$NR$^6$R$^7$.

Other examples of preferred compounds of the formula I are those wherein ring A is benzo, R$^1$ is fluoro, ring B is 2-pyridyl or phenyl and R$^3$ is cyano.

Other examples of preferred compounds of the formula I are those wherein ring B is phenyl or 2-pyridyl.

Other more specific embodiments of this invention are the following:

(a) compounds of the formula I wherein ring A is benzo;
(b) compounds of the formula I wherein ring A is thieno;
(c) compounds of the formula I wherein ring B is phenyl;
(d) compounds of the formula I wherein ring B is a pyridyl or pyrimidyl;
(e) compounds of the formula I wherein the bond represented by both solid and dashed lines is a single carbon-carbon bond;
(f) compounds of the formula I wherein the bond represented by both solid and dashed lines is a double carbon-carbon bond; and
(g) compounds of the formula I wherein R$^3$ is fluoro, cyano, hydrogen or —CH$_2$NR$^6$R$^7$ wherein R$^6$ and R$^7$, together with the nitrogen to which they are attached, form a morpholine, pyrrolidine or piperazine ring.

Examples of specific compounds of the formula I are:

3-(6-Chloro-2-chloro-phenyl)-2-[2-hydroxy-2-(6-methyl-pyridin-2-yl)-vinyl]-3H-quinazolin-4-one;

2-{2-[3-(2-Chloro-phenyl)-4-oxo-3,4-dihydro-quinazolin-2-yl]-1-hydroxy-vinyl}-nicotinonitrile;

2-{2-[3-(2-Chloro-pyrid-3-yl)-6-fluoro-4-oxo-3,4-dihydro-quinazolin-2-yl]-1-hydroxy-vinyl}-nicotinonitrile;

2-{2-[6-Chloro-3-(2-methyl-phenyl)-4-oxo-3,4-dihydro-quinazolin-2-yl]-1-hydroxy-vinyl}-nicotinonitrile;

3-(2-Chloro-phenyl)-2-[2-(3-diethylaminomethyl-phenyl)-2-hydroxy-ethyl]-6-fluoro-3H-quinazolin-4-one;

3-(2-Chloro-phenyl)-6-fluoro-2-[2-(3-pyrrolidin-1-ylmethyl-phenyl)-2-hydroxy-ethyl]-3H-quinazolin-4-one;

3-(2-Chloro-pyrid-3-yl)-2-[2-(3-diethylaminomethyl-phenyl)-2-hydroxy-ethyl]-6-fluoro-3H-quinazolin-4-one;

2-[2-(3-Diethylaminomethyl-phenyl)-2-hydroxy-ethyl]-6-fluoro-3-(2-fluoro-phenyl)-3H-quinazolin-4-one;

2-[2-(3-Diethylaminomethyl-phenyl)-2-hydroxy-ethyl]-3-(2-fluoro-phenyl)-3H-quinazolin-4-one;

2-{2-[3-(2-Chloro-pyrid-3-yl)-6-fluoro-4-oxo-3,4-dihydro-quinazolin-2-yl]-1-hydroxy-vinyl}-6-methyl-nicotinonitrile;

2-{2-[3-(2-Chloro-phenyl)-4-oxo-3,4-dihydro-quinazolin-2-yl]-1-hydroxy-vinyl}-6-methyl-nicotinonitrile;

2-{2-[6-Chloro-3-(2-chloro-phenyl)-4-oxo-3,4-dihydro-quinazolin-2-yl]-1-hydroxy-vinyl}-6-methyl-nicotinonitrile;

2-{2-[3-(2-Chloro-phenyl)-6-fluoro-4-oxo-3,4-dihydro-quinazolin-2-yl]-1-hydroxy-vinyl}-6-fluoro-nicotinonitrile;

2-{2-[3-(2-Chloro-phenyl)-6-fluoro-4-oxo-3,4-dihydro-quinazolin-2-yl]-1-hydroxy-vinyl}-4-fluoro-benzonitrile;

2-{2-[3-(2-Chloro-phenyl)-6-fluoro-4-oxo-3,4-dihydro-quinazolin-2-yl]-1-hydroxy-vinyl}-4-methyl-benzonitrile;

2-{2-[3-(2-Chloro-phenyl)-4-oxo-3,4dihydro-thieno[3,2-d]pyrimidin-2-yl]-1-hydroxy-vinyl}-6-methyl-nicotinonitrile;

2-{2-[3-(2-methyl-phenyl)-4-oxo-3,4-dihydro-thieno[3,2-d]pyrimidin-2-yl]-1-hydroxy-vinyl}-6-methyl-nicotinonitrile;

2-{2-[3-(2-Chloro-pyrid-3yl)-4-oxo-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-4-fluoro-benzonitrile;

2-{2-[3-(2-Fluoro-phenyl)-4oxo-3,4-dihydro-thieno[3,2-d]pyrimidin-2-yl]-1-hydroxy-vinyl}-4-methyl-benzonitrile;

2-{2-[3-(2-Chloro-phenyl)-4-oxo-3,4-dihydro-thieno[3,2-d]pyrimidin-2-yl]-1-hydroxy-vinyl}-benzonitrile; and 2-{2-[3-(2-Chloro-pyrid-3yl)-4-oxo-3,4-dihydro-thieno[3,2-d]pyrimidin-2-yl]-1-hydroxy-vinyl}-benzonitrile.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising an amount of a compound of formula I that is effective in treating such condition and a pharmaceutically acceptable carrier.

This invention also relates to a method of treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal in need of such treatment an amount of a compound of formula I that is effective in treating such condition.

This invention also relates to a pharmaceutical composition for treating a disorder or condition, the treatment or prevention of which can be effected or facilitated by reducing or inhibiting glutamate neurotransmission in a mammal, comprising an amount of a compound of formula I, or a pharmaceutically effective salt thereof, that is effective in treating such disorder or condition and a pharmaceutically acceptable carrier.

This invention also relates to a method of treating a disorder or condition, the treatment of which can be effected or facilitated by reducing or inhibiting glutamate neurotransmission in a mammal, comprising administering to a mammal in need of such treatment an amount of a compound of formula I, or a pharmaceutically effective salt thereof, that is effective in treating such disorder or condition.

This invention also relates to a pharmaceutical composition for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising an AMPA receptor antagonizing effective amount of a compound of formula I, or a pharmaceutically salt thereof, and a pharmaceutically acceptable carrier.

This invention also relates to a method for treating a condition selected from stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal requiring such treatment an AMPA receptor antagonizing effective amount of a compound of formula I, or a pharmaceutically acceptable salt thereof.

This invention also relates to a pharmaceutical composition for treating a disorder or condition, the treatment of which can be effected or facilitated by reducing or inhibiting glutamate neurotransmission in a mammal, comprising an AMPA receptor antagonizing effective amount of a compound of formula I, or a pharmaceutically acceptable salt thereof, and a pharmaceutically acceptable carrier.

This invention also relates to a method for treating a disorder or condition, the treatment of which can be effected or facilitated by reducing or inhibiting glutamate neurotransmission in a mammal, comprising administering to a mammal requiring such treatment an AMPA receptor antagonizing effective amount of a compound of formula I or a pharmaceutically acceptable salt thereof.

Unless otherwise indicated, the alkyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties.

The term "treating" as used herein, refers to reversing, alleviating, inhibiting the progress of, or preventing the disorder or condition to which such term applies, or one or more symptoms of such disorder or condition. The term "treatment", as used herein, refers to the act of treating, as "treating" is defined immediately above.

Unless otherwise indicated, "halo" and "halogen", as used herein, refer to fluorine, bromine, chlorine or iodine.

Compounds of the formula I may have chiral centers and therefore may exist in different enantiomeric and diastereomic forms. This invention relates to all optical isomers and all stereoisomers of compounds of the formula I and mixtures thereof, and to all pharmaceutical compositions and methods of treatment defined above that contain or employ them, respectively.

Due to the substituent at position "2" and the carbonyl groups at position "4" in the quinazolin-4-one of formula I, the ring attached to the nitrogen at position "3" cannot rotate freely. This restricted rotation means that compounds of the formula I exist in two isomeric forms or atropisomers. These atropisomers can be separated.

This invention includes, for example, those stereoisomers of compounds of the formula I that are atropisomers. Atropisomers are isomeric compounds that are chiral, i.e., each isomer is not superimposable on its mirror image and the isomers, once separated, rotate polarized light in equal but opposite directions. Atropisomers are distinguished from onantiomers in that atropisomers do not possess a single asymmetric atom. Such compounds are conformational isomers which occur when rotation about a single bond in the molecule is prevented or greatly slowed as a result of steric interactions with other parts of the molecule and the substituents at both ends of the single bond are unsymmetrical. A detailed account of atropisomers can be found in Jerry March, *Advanced Organic Chemistry* 101–102 (4th ed. 1992) and in Oki, *Top,* Stereochem., 14, 1–81 (1983).

The following structure depicts the atropisomerism of the compound of formula I.

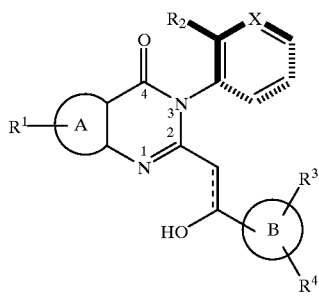

Ia

The bold lines in formulae Ia indicate that the bolded atoms, and the groups attached thereto, are sterically restricted so as to exist orthogonally above the plane of the quinazolinone ring. This steric restriction is due to a rotational energy barrier preventing free rotation about the single bond connecting the nitrogen at position "3" of the quinazolinone ring to the X-containing aryl (phenyl or pyridyl) group.

Those compounds of the formula I in which the bond represented by both solid and dashed lines is a single carbon-carbon bond will contain at least one chiral center in addition to the one giving use to atropisomerism. Such compounds, therefore, will exist in at least four stereoisomeric forms.

Formulas I and Ia above include compounds identical to those depicted but for the fact that one or more hydrogen, carbon or other atoms are replaced by isotopes thereof. Such compounds may be useful as research and diagnostic tools in metabolism pharmacokinetic studies and in binding assays.

Formulas I and Ia above include compounds identical to those depicted but for the fact that one or more hydrogen or carbon atoms are replaced by isotopes thereof. Such compounds are useful as research and diagnostic tools in metabolism pharmokinetic studies and in binding assays. Specific applications in research include radioligand binding assays, autoradiography studies and in vivo binding studies.

DETAILED DESCRIPTION OF THE INVENTION

The compounds of formula I can be prepared according to the methods of Scheme 1. In the reaction Scheme and discussion that follow, unless otherwise indicated, rings A and B and substituents $R^1$ through $R^7$, are defined as above for formula I.

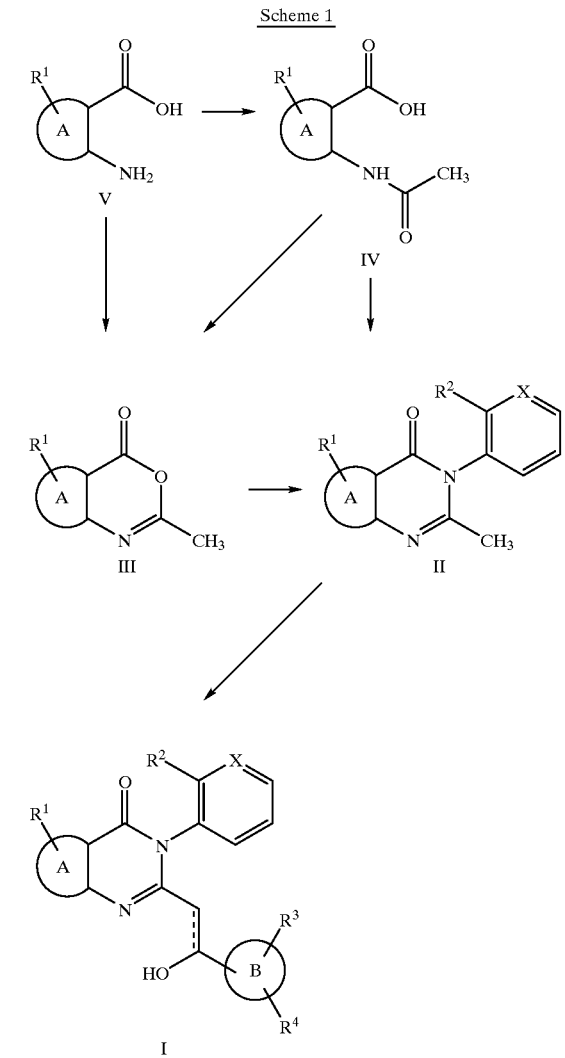

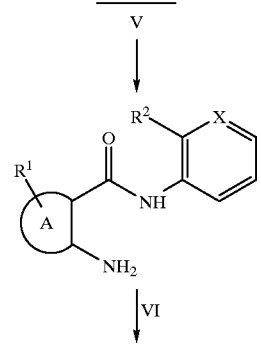

-continued

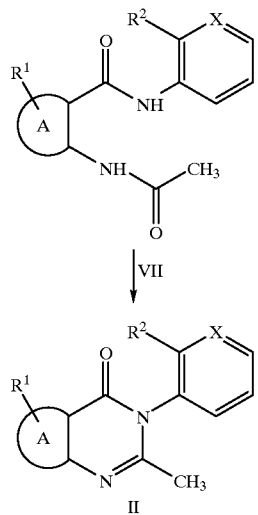

II

Scheme 1 illustrates methods of synthesizing compounds of the formula I. Referring to Scheme 1, a compound of the formula V can be converted into an acetamide of the formula IV by reaction with acetyl chloride or acetic anhydride in the presence of a base in a reaction inert solvent. Suitable solvents include methylene chloride, dimethoxethane (DME), t-butyl methyl ether, dichloroethane, tetrahydrofuran (THF) and dioxane. Suitable bases include trialkylamines such as triethylamine and tributylamine, dimethylaminopyridine and potassium carbonate, preferably triethylamine. The temperature of this reaction can range from about 0° C. to about 100° C. and the reactions generally allowed to run for about 1 hour to about 10 hours. Preferably, the reaction is carried at about 0° C. to 30° C. for about 3 hours.

The acetamide of formula IV can be cyclized to form a compound of the formula III by reaction with a dehydrating agent, in the presence of a catalyst, in a dry reaction inert solvent. Suitable dehydrating agents include acetic anhydride, phosphorus pentoxide, dicyclohexylcarbodiimide and acetyl chloride. Acetic anhydride is preferred. Suitable catalysts include sodium or potassium acetate, acetic acid, p-toluene sulfonic acid, and boron trifluoride etherate. Sodium acetate is preferred. Suitable solvents include dioxane, toluene, diglyme and dichloroethane. The temperature for this reaction can range from about 0° C to about 150° C. and the reaction is typically carried at for about 1 hour to about 24 hours. Preferably, the reaction is conducted in dioxane at about 80° C. to 120° C. for about 3 to 10 hours.

Alternatively, the compound of formula V can be converted directly into a compound of formula III by reacting it with acetic anhydride in the presence of an acid catalyst in a reaction inert solvent. Examples of acid catalysts that can be used are acetic acid, sulfuric acid, and p-toluene sulfonic acid. Acetic acid is preferred. Examples of solvents that can be used are toluene and xylene. Acetic acid is also the preferred solvent. The temperature of the reaction mixture can range from about 20° C. to about 150° C. Typically, the mixture is allowed to react for about 10 minutes to about 10 hours. The reaction is preferably carried out at about 80° C. to 120° C. for about 2 to 5 hours.

The compound of formula III, formed by either of the above methods, can then be reacted with an amine of the formula

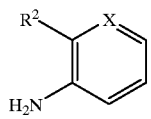

VIII in a polar protic solvent, in the presence of an acid catalyst, to form compound of formula II. Suitable acid catalysts include acetic acid, p-toluene sulfonic acid and sulfuric acid, with acetic acid being preferred. Suitable polar protic solvents include acetic acid, methanol, ethanol and isopropanol, with acetic acid being preferred. This reaction is generally carried out at a temperature from about 20° C. to about 150° C. for about 1 hour to about 24 hours, preferably at about 80° C. to 120° C. for about 6 hours.

Alternatively, a compound of the formula IV can be converted directly into a compound of the formula II by reacting it with a dehydrating agent, an amine of the formula VII, as described above, and a base, in a reaction inert solvent. Examples of dehydrating agents that can be used are phosphorous trichloride, phosphorous oxychloride, phosphorous pentachloride and thionyl chloride, with phosphorous trichloride being preferred. Suitable bases include pyridine, diisopropylamine, lutidine, dimethylaminopyridine, triethylamine and N-methyl morpholine. Examples of solvents that can be used are toluene, dioxane, THF, chlorobenzene, DME, cyclohexane, benzene and xylene. Preferably, pyridine is used as the base and the reaction is carried out in a toluene solvent. Under some circumstances, when the combined reactants are a liquid, the reaction may be run neat. The temperature can range from about 50° C. to about 150° C. and the reaction mixture is generally allowed to react for about 1 hour to about 24 hours, the reaction is preferably conducted at about 80° C. to 120° C. for about 2 to 8 hours.

The compound of formula II is then deprotonated with a strong base such as lithium diisopropylamide (LDA), lithium diethylamide, sodium hydride, or lithium or sodium hexamethyidisilylazide (LiHMDS or NaHMDS), preferably LDA or LiHMDS, in a suitable solvent such as THF, ether, dioxane or DME, preferably ether or THF, at a temperature from about −100° C. to about 100° C., preferably between about −80° C. and −50° C. The anion thus formed is reacted with an aldehyde of the formula IX or an ester of the formula X,

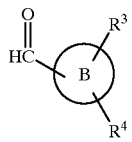

IX

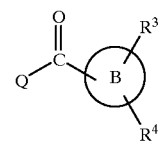

X wherein Q is a group that facilitates nucleophilic addition to the carbonyl group of formula X (e.g., $OR^8$ or $SR^8$, wherein $R^8$ is methyl, ethyl, phenyl or 2-pyridyl) to form a compound of the formula I.

The compound of formula IX or X can be added to the anion solution (normal addition) or the anion solution can be added to the compound of formula IX or X (inverse addition). While both methods can be used to produce compounds of the formula I, inverse addition is preferred. Also, when sodium hydride is used as the base and the resulting anion is reacted with a compound of the formula X, the preferred reaction temperature is from about 0° C. to about 80° C. and the reagents having formulas II and X can be combined in the reaction mixture at the same time or in the normal addition mode. (See *J Med. Chem.*, 1990, 33, 161).

Alternatively, a compound of the formula V can be converted to a compound of the formula II according to the methods described in Scheme 2. The compound of formula II, so formed, can then be converted into the desired compound of formula I according to the methods of Scheme 1. Referring to Scheme 2, a compound of the formula V is reacted with a coupling reagent, an amine of the formula VIII, as described above, and a base in a reaction inert solvent to form a compound of the formula VI. Examples of suitable coupling reagents that activate the carboxylic functionality are dicyclohexylcarbodiimide, N-3-dimethylaminopropyl-N'-ethylcarbodiimide, 2-ethoxy-1-ethoxycarbonyl-1,2-dihydroquinoline (EEDQ), carbonyl diimidazole (CDI), and diethylphosphorylcyanide. Suitable bases include dimethylaminopyridine (DMAP) and triethylamine. Dimethylaminopyridine is preferred. A catalyst such as hydroxybenzotriazole (HBT) may be used. The coupling is conducted in an inert solvent, preferably an aprotic solvent. Suitable solvents include acetonitrile, dichloromethane, dichloroethane, and dimethylformamide. The preferred solvent is dichloromethane. The temperature of the aforesaid reaction is generally from about −30 to about 80° C., and is preferably about 0 to about 25° C.

The compound of formula VI can be converted into a compound of the formula VII by reaction with acetyl chloride or acetic anhydride in the presence of a base (e.g., a trialkylamine such as triethylamine or tributylamine, dimethylaminopyridine or potassium carbonate) in a reaction inert solvent. Suitable solvents include methylene chloride, tetrahydrofuran and chloroform, preferably methylene chloride. Preferably, triethylamine is used as the base. This reaction is generally carried at a temperature from about 0° C. to about 50° C. for about 1 hour to about 10 hours, preferably at about ambient temperature for about 3 hours.

The compound of formula VII is cyclized to a compound of formula II by reaction with triphenylphosphine, a base, and a dialkyl azodicarboxylate in a reaction inert solvent. Examples of bases that can be used in this reaction are pyridine, triethylamine and 4-dimethylaminopyridine, with 4-dimethylaminopyridine being preferred. Appropriate solvents include dimethylformamide, toluene, xylene, tetrahydrofuran and dioxane, with dioxane being preferred. Typically, this reaction is conducted at a temperature from about 25° C. to about 125° C. for about 1 hour to about 24 hours, preferably at about 100° C. for about 8 to 15 hours.

Compounds of formula II can also be made according to the methods described in Miyashita, et al., *Heterocycles*, 42, 2, 691–699 (1996).

Unless indicated otherwise, the pressure of each of the above reactions is not critical. Generally, the reactions will be conducted at a pressure of about one to about three atmospheres, preferably at ambient pressure (about one atmosphere)

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts, i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate, methanesulfonate and pamoate [i.e., 1,1'-methylene-bis-(2-hydroxy-3-naphthoate)] salts.

The compounds of the formula I and the pharmaceutically acceptable salts thereof (hereinafter, also referred to as the active compounds of the invention) are useful for the treatment of neurodegenerative, psychotropic and drug or alcohol induced deficits and are potent AMPA receptor antagonists. The active compounds of the invention may therefore be used in the treatment or prevention of stroke, cerebral ischemia, spinal cord trauma, head trauma, Alzheimer's Disease, Huntington's Chorea, amyotrophic lateral sclerosis, epilepsy, AIDS-induced dementia, muscular spasms, migraine headaches, urinary incontinence, psychosis, convulsions, perinatal hypoxia, hypoxia (such as conditions caused by strangulation, surgery, smoke inhalation, asphyxiation, drowning, choking, electrocution or drug or alcohol overdose), cardiac arrest, hypoglycemic neuronal damage, opiate tolerance, addiction withdrawal (such as alcoholism and drug addiction including opiate, cocaine and nicotine addiction), ocular damage, retinopathy, retinal neuropathy, tinnitus, idiopathic and drug induced Parkinson's Disease, anxiety, emesis, brain edema, chronic or acute pain, tardive dyskinesia and cerebral deficits subsequent to cardiac bypass surgery and grafting.

The in vitro and in vivo activity of the compounds of the invention for AMPA receptor antagonism can be determined by methods available to one of ordinary skill in the art. One method for determining the activity of the compounds of the invention is by inhibition of pentylenetetrazol (PTZ)-induced seizures. Another method for determining the activity of the compounds of the invention is by blockade of AMPA receptor activation-induced $^{45}Ca^{2+}$ uptake.

One specific method for determining inhibition of pentylenetetrazol (PTZ)-induced seizures is as follows. The activity of the compounds of the invention for inhibition of pentylenetetrazol (PTZ)-induced seizures in mice can be determined according to the following procedure. This assay examines the ability of compounds to block seizures and death produced by PTZ. Measures taken are latency to clonic and tonic seizures, and death. $ID_{50}s$ are determined based on percent protection.

Male CD-1 mice from Charles River, weighing 14–16 g on arrival and 25–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

Mice are administered the test compounds or vehicle (i.p., s.c., or p.o.) and are placed into plexiglass cages in groups of five. At a predetermined time after these injections, mice are given an injection of PTZ (i.p., 120 mg/kg) and placed into individual plexiglass cages. Measures taken during this five minute test period are: (1) latency to clonic seizures, (2) latency to tonic seizures, and (3) latency to death. Treatment groups are compared to the vehicle-treated group by Kruskal-Wallis Anova and Mann-Whitney U tests (Statview). Percent protection is calculated for each group (number of subjects not showing seizure or death as indicated by a score of 300 secs) at each measure. $ID_{50}$'s are determined by prohibit analysis (Biostat).

Another method for determining the activity of the compounds is to determine the effect of the compounds on motor coordination in mice. This activity can be determined according to the following procedure.

Male CD-1 mice from Charles River, weighing 14–16 g on arrival and 23–35 g at the time of testing, serve as subjects for these experiments. Mice are housed 13 per cage under standard laboratory conditions on a L:D/7 a.m.: 7 p.m. lighting cycle for at least 7 days prior to experimentation. Food and water are available ad libitum until the time of testing.

All compounds are administered in a volume of 10 ml/kg. Drug vehicles will depend on compound solubility, but screening will typically be done using saline, distilled water, or E:D:S/5:5:90 (5% emulphor, 5% DMSO, and 90% saline) as the injection vehicle.

The apparatus used in these studies consists of a group of five 13.34×13.34 cm wire mesh squares suspended on 11.43 cm steel poles connected to a 165.1 cm pole which is elevated 38.1 cm above the lab bench. These wire mesh squares can be turned upside-down.

Mice are administered test compounds or vehicle (i.p., s.c., or p.o) and are placed into plexiglass cages in groups of five. At a predetermined time after these injections, mice are placed on top of the wire mesh squares and flipped so that they are suspended upside-down. During the one minute test, mice are rated 0 if they fall off the screen, 1 if they hang on upside-own, or 2 if they climb up onto the top. Treatment groups are compared to the vehicle-treated group with Kruskal-Wallis and Mann-Whitney U tests (Statview).

One specific method for determining blockade of AMPA receptor activation-induced $^{45}Ca^{2+}$ uptake is described below.

Neuronal primary cultures

Primary cultures of rat cerebellar granule neurons are prepared as described by Parks, T. N., Artman, L. D., Alasti, N., and Nemeth, E. F., *Modulation Of N-Methyl-D-Aspartate Receptor-Mediated Increases In Cytosolic Calcium In Cultured Rat Cerebellar Granule Cells*, Brain Res. 552, 13–22 (1991). According to this method, cerebella are removed from 8 day old CD rats, minced into 1 mm pieces and incubated for 15 minutes at 37° C. in calcium-magnesium free Tyrode's solution containing 0.1% trypsin. The tissue is then triturated using a fine bore Pasteur pipette. The cell suspension is plated onto poly-D-lysine coated 96-well tissue culture plates at $10^5$ cells per well. Medium consists of Minimal Essential Medium (MEM), with Earle's salts, 10% heat inactivated Fetal Bovine Serum, 2 mM L-glutamine, 21 mM glucose, Penicillin-Streptomycin (100 units per ml) and 25 mM KCl. After 24 hours, the medium is replaced with fresh medium containing 10 µM cytosine arabinoside to inhibit cell division. Cultures should be used at 6–8 DIV.

AMPA receptor activation-induced $^{45}Ca^{2+}$ uptake

The effects of drugs on AMPA receptor activation-induced $^{45}Ca^{2+}$ uptake can be examined in rat cerebellar granule cell cultures. Cultures in 96 well plates are preincubated for approximately 3 hours in serum free medium and then for 10 minutes in a $Mg^{2+}$-free balanced salt solution (in mM: 120 NaCl, 5 KCl, 0.33 $NaH_2PO_4$ 1.8 $CaCl_2$, 22.0 glucose and 10.0 HEPES at pH 7.4) containing 0.5 mM DTT, 10 uM glycine and drugs at 2× final concentration. The reaction is started by rapid addition of an equal volume of the balanced salt solution containing 100 µM of the AMPA receptor agonist kainic acid and $^{45}Ca^{2+}$ (final specific activity 250 Ci/mmol). After 10 minutes at 25° C., the reaction is stopped by aspirating the $^{45}Ca^{2+}$-containing solution and washing the cells 5× in an ice cold balanced salt solution containing no added calcium and 0.5 mM EDTA. Cells are then lysed by overnight incubation in 0.1% Triton-X100 and radioactivity in the lysate is then determined. All of the compounds of the invention, that were tested, had $IC_{50}$s of less than 5 µM.

The compositions of the present invention may be formulated in a conventional manner using one or more pharmaceutically acceptable carriers. Thus, the active compounds of the invention may be formulated for oral, buccal, transdermal (e.g., patch), intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycollate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., stroke) is 0.01 to 50 mg/kg of the active ingredient per unit dose which could be administered, for example, 1 to 4 times per day.

Aerosol formulations for treatment of the conditions referred to above (e.g., stroke) in the average adult human are preferably arranged so that each metered dose or "puff" of aerosol contains 20 $\mu$g to 1000 $\mu$g of the compound of the invention. The overall daily dose with an aerosol will be within the range 100 $\mu$g to 10 mg. Administration may be several times daily, for example 2, 3, 4 or 8 times, giving for example, 1, 2 or 3 doses each time.

The following Examples illustrate the preparation of the compounds of the present invention. Commercial reagents were utilized without further purification. Melting points are uncorrected. All NMR data were recorded at 250, 300 or 400 MHz in deuterochloroform unless otherwise specified and are reported in parts per million ($\delta$) and are referenced to the deuterium lock signal from the sample solvent. All non-aqueous reactions were carried out in dry glassware with dry solvents under an inert atmosphere for convenience and to maximize yields. All reactions were stirred with a magnetic stirring bar unless otherwise stated. Unless otherwise stated, all mass spectra were obtained using chemical impact conditions. Ambient or room temperature refers to 20–25° C. Melting points are uncorrected.

EXAMPLE 1

3-(2-Chloro-phenyl)-6-fluoro-2-(2-hydroxy-2-pyridin-2-yl-vinyl)-3H-quinazolin-4-one A solution of diisopropylamine (0.061 mL, 0.47 mmol) in tetrahydrofuran (2.7 mL) was chilled to −78° C. and butyllithium (0.134 mL, 0.34 mmol, 2.5 N in hexanes) was added dropwise. The solution was stirred 20 min and then a solution 3-(2-chloro-phenyl)-6-fluoro-2-methyl-3H-quinazolin-4-one (0.10 g, 0.35 mmol) in tetrahydrofuran (0.7 mL) was added dropwise. The solution became intense red and was stirred 30 min. In a separate vessel a solution of ethyl picolinate (0.491 mL, 3.6 mmol) in tetrahydrofuran (2 mL) was prepared and chilled to −78° C. The cold red anion solution was added to the cold ethyl picolinate solution via canula over a two minute period. The resulting mixture was stirred 30 minutes at −78° C. and then was allowed to warm to ambient temperature. The reaction was quenched with water. The mixture was repeatedly extracted with ethyl acetate. The combined extracts were washed with water and brine, dried over magnesium sulfate and concentrated. The residue was triturated with ether/hexane and the yellow solid which formed was collected and dried to yield 0.054 g (40%) of 3-(2-chloro-phenyl)-6-fluoro-2-(2-hydroxy-2-pyridin-2-yl-vinyl)-3H-quinazolin-4-one which had: mp>250° C. $^1$H NMR (DMSO$_d$) $\delta$8.45 (d, J=5 Hz, 1 H), 7.97 (d, J=7 Hz, 1 H), 7.90 (dt, J=1, 8 Hz, 1 H), 7.88-7.58 (m, 7 H), 7.35 (sym m, 1 H), 5.80 (s, 1 H). Analysis calculated for $C_{21}H_{13}ClFN_3O_2$: C, 64.05; H, 3.33; N, 10.67. Found: C, 64.16; H, 3.71; N, 10.72.

EXAMPLE 2

2-{2-[6-Fluoro-3-(2-methyl-pyridin-3-yl)-4-oxo-3,4-dihydro-quinazolin-2-yl]-1-hydroxy-vinyl}-benzonitrile A solution of diisopropylamine (0.046 mL, 0.47 mmol) in tetrahydrofuran (2.7 mL) was chilled to −78° C. and butyllithium (0.13 mL, 0.32 mmol, 2.5 N in hexanes) was added dropwise. The solution was stirred 10 minutes and then a solution 6-fluoro-2-methyl-3-(2-methyl-pyridin-3-yl)-3H-quinazolin-4-one (0.10 g, 0.37 mmol) in tetrahydrofuran (0.7 mL) was added dropwise. The solution became intense red and was stirred 30 minutes. In a separate vessel a solution of methyl 2-cyanobenzoate (0.50 g, 3.1 mmol) in tetrahydrofuran (10 mL) was prepared and chilled to −78° C. The cold red anion solution was added to the cold methyl 2-cyanobenzoate solution via canula over 30 seconds. The resulting mixture was stirred 30 minutes at −78° C. and then quenched with saturated aqueous bicarbonate and warmed to ambient temperature. The mixture was diluted with water and repeatedly extracted with ethyl acetate. The combined extracts were washed with water and brine, dried over magnesium sulfate and concentrated. The residue was flash chromatographed on silica gel (20×100 mm) with elution proceeding as follows: 10% ethyl acetate/hexane (50 mL), nil; 20% ethyl acetate/hexane (50 mL), unweighedrecovered 3-(2-methyl-pyridin-3-yl)-6-fluoro-2-methyl-3H-quinazolin-4-one; 30% ethyl acetate/hexane (50 mL), nil; 40% ethyl acetate/hexane (50 mL), unweighed recovered methyl 2-cyanobenzoate; 50% ethyl acetate/hexane (50 mL), unweighed impurity; 60% ethyl acetate/hexane (50 mL), mixture of impurity and desired product; 70% ethyl acetate/hexane (50 mL), product. The product containing fractions were combined and concentrated. The residue was triturated with 1% ethyl acetate/ether and the yellow solid which formed was collected and dried to yield 0.017 g (10%) of 2-{2-[6-fluoro-3-(2-methyl-pyridin-3-yl)-4-oxo-3,4-dihydro-quinazolin-2-yl]-1-hydroxy-vinyl}-benzonitrile which had: mp 213–215° C.; $^1$H NMR $\delta$8.70 (d, J=4 Hz, 1 H), 7.85 (dd, J=3, 8 Hz, 1 H), 7.67 (d, J=7 Hz, 1 H), 7.60 (d, J=9 Hz, 1 H), 7.58-7.38 (m, 6 H), 4.94 (s, 1 H), 2.44 (s, 3 H). Analysis calculated for $C_{23}H_{15}FN_4O_2 \cdot 0.25$ $H_2O$: C, 68.57; H, 3.88; N, 13.91. Found: C, 68.52, 68,91; H, 4.13, 4.21; N, 13.25, 13.28.

EXAMPLE 3

2-{2-[3-(2-Chloro-pyridin-3-yl)-6-fluoro-4-oxo-3,4-dihydro-quinazolin-2-yl]-1-hydroxy-vinyl}-benzonitrile Two identical reactions were run side by side. A solution of diisopropylamine (0.120 mL, 0.91 mmol) in tetrahydrofuran (5.4 mL) was chilled to −78° C. and butyllithium (0.26 mL, 0.65 mmol, 2.5 N in hexanes) was added dropwise. The solution was stirred 10 minutes and then a solution 3-(2-chloro-pyridin-3-yl)-6-fluoro-2-methyl-3H-quinazolin-4-one (0.204 g, 0.70 mmol) in tetrahydrofuran (5 mL) was added dropwise. The solution became intense red and was stirred 30 minutes. In a separate vessel a solution of methyl 2-cyanobenzoate (1.02 g, 6.33 mmol) in tetrahydrofuran (15 mL) was prepared and chilled to −78° C. The cold red anion solution was added to the cold methyl 2-cyanobenzoate solution via canula over 30 seconds. The resulting mixture was stirred 1 hour at −78° C. and then quenched with saturated aqueous bicarbonate and warmed to ambient temperature. The mixture was diluted with water and repeatedly extracted with ethyl acetate. The combined extracts were washed with water and brine, dried over magnesium sulfate and concentrated. The residues from the two side by side reactions were combined and flash chromatographed on silica gel (40×220 mm) with elution proceeding as follows: 10% ethyl acetate/hexane (250 mL), nil; 20% ethyl acetate/hexane (250 mL), nil; 30% ethyl acetate/hexane (50 mL), unweighed impurity; 40% ethyl acetate/hexane (250 mL), unweighed recovered 3-(2-chloro-pyridin-3-yl)-6-fluoro-2-methyl-3H-quinazolin-4-one; 50% ethyl acetate/hexane (250 mL), nil; 60% ethyl acetate/hexane (250 mL), desired product (tlc $R_f$=0.3 with 50% ethyl acetate/hexane on silica gel). The product containing fractions were combined and concentrated. The residue was triturated with ether and the light yellow solid which formed was collected and dried to yield 0.093 g (17%) of 2-{2-[6-fluoro-3-(2-methyl-pyridin-3-yl)-4-oxo-3,4-dihydro-quinazolin-2-yl]-1-hydroxy-vinyl}-benzonitrile which had: mp 217–218° C.; $^1$H NMR δ8.60 (dd, J=3, 5 Hz, 1 H), 7.85 (dd, J=3, 8 Hz, 1 H), 7.81 (dd, J=2, 8 Hz, 1 H), 7.67 (d, J=7 Hz, 1 H), 7.58-7.42 (m, 6 H), 4.98 (s, 1 H). Analysis calculated for $C_{21}H_{12}ClFN_4O_2$: C, 63.09; H, 2.89; N, 13.38. Found: C, 62.90; H, 2.81; N, 13.01.

The title compounds of Example 4–10 in the table below were prepared following substantially the same procedures employed in Examples 1–3 above.

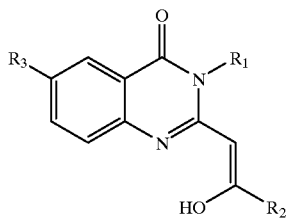

| EX. | $R^3$ | $R^2$ | $R^1$ | Physical properties |
|---|---|---|---|---|
| 4 | F | 2-methyl-thiazol-4-yl | 2-chlorophenyl | mp 245–247° C. $^1$H NMR (DMSO$_{d6}$) δ 7.99 (s, 1H), 7.81–7.59 (m, 8H), 5.40 (s, 1H), 2.50 (s, 3 H). Analysis calculated for $C_{20}H_{13}ClFN_3O_2S$: C, 58.04; H, 3.17; N, 10.15. Found: C, 57.87; H, 3.41; N, 10.27. |
| 5 | F | 6-methyl-pyrid-2-yl | 2-chlorophenyl | mp 231–232° C. $^1$H NMR δ 7.83 (dd, J=3, 9Hz, 1H), 7.76 (d, J=9Hz, 1 H), 7.67–7.62 (m, 1 H), 7.60 (d, J=8 Hz, 1H), 7.56–7.48 (sym m, 2H), 7.46–7.40 (m, 2H), 7.38 (dd, J=4.5, 9Hz, 1 H), 7.11 (d, J=8 Hz, 1H), 5.95 (s, 1 H), 2.38 (s, 3H). Analysis calculated for $C_{22}H_{15}ClFN_3O_2$·0.25H$_2$O: C, 64.08; H, 3.79; N, 10.19. Found: C, 64.26; H, 3.70; N, 10.16. |
| 6 | F | 3-cyano-6-methyl-pyrid-2-yl | 2-chlorophenyl | mp > 260° C. $^1$H NMR δ 7.91 (d, J=8Hz, 1H), 7.85 (dd, J=2, 8Hz, 1 H), 7.68–7.64 (sym m, 1H), 7.58–7.50 (sym m, 2H), 7.50–7.40 (m, 3H), 7.23 (d, J=8Hz, 1H), 5.81 (s, 1H), 2.44 (s, 3H). Analysis calculated for $C_{23}H_{14}ClFN_4O_2$·0.25 H$_2$O: C, 63.17; H, 3.34; N, 12.81. Found: C, 63.10; H, 3.31; N, 12.72. |
| 7 | F | 3-cyanopyrid-2-yl | 2-chlorophenyl | mp > 250° C. $^1$H NMR δ 8.58 (d, J=5Hz, 1H), 8.05 (dd, J=2, 8Hz, 1 H), 7.84–7.81 (m, 1 H), 7.65 (m, 1H), 7.58–7.50 (sym m, 2 H), 7.50–7.44 (m, 2 H), 7.42–7.38 (m, 2 H), 5.79 (s, 1H). Analysis calculated for $C_{22}H_{12}ClFN_4O_2$·0.25 H$_2$O: C, 62.42; H, 2.98; N, 13.24. Found: C, 62.03; H, 2.78; N, 13.00. |
| 8 | F | 2-cyanophenyl | 2-chlorophenyl | mp 211–212° C. $^1$H NMR δ 7.84 (dd, J=3, 9Hz, 1H), 7.67 (d, J=8Hz, 1 H), 7.65–7.62 (m, 1 H), 7.56–7.38 (m, 8 H), 5.00 (s, 1H). Analysis calculated for $C_{23}H_{13}ClFN_3O_2$·0.75 H$_2$O: C, 64.04; H, 3.39; N, 9.74. Found: C, 64.16; H, 3.11; N, 9.72. |
| 9 | F | 3-cyanopyrid-2-yl | 2-chloropyrid-3-yl | mp > 250° C. $^1$H NMR δ 8.67–8.57 (m, 2H), 8.07 (d, J=8Hz, 1H), 7.85 (d, J=8Hz, 1 H), 7.79 (d, J=8 Hz, 1H), 7.60–7.40 (m, 4H), 5.78 (s, 1 H). |

-continued

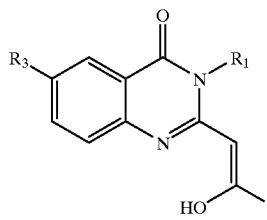

| EX. | R³ | R² | R¹ | Physical properties |
|---|---|---|---|---|
| 10 | F | 3-cyano-6-methyl-pyrid-2-yl | 2-chloropyrid-3-yl | p > 250° C.<br>¹N HMR δ 8.63 (d, J=5Hz, 1H), 7.92 (d, J=8Hz, 1H), 7.87–7.78 (m, 2H), 7.53 (dd, J=5, 8 Hz, 1H), 7.51–7.44 (m, 2H), 7.24 (d, J=8Hz, 1H), 5.76 (s, 1H), 2.46 (s, 3 H). |

EXAMPLE 11

Two diastereomers of 3-(2-chloro-phenyl)-6-fluoro-2-[2-(2-fluoro-phenyl)-2-hydroxy-ethyl]-3H-quinazolin-4-one A solution of diisopropylamine (0.60 mL, 4.57 mmol) in tetrahydrofuran (27 mL) was chilled to −78° C. and butyl-lithium (1.30 mL, 3.25 mmol, 2.5 N in hexanes) was added dropwise. The solution was stirred 10 minutes and then a solution 3-(2-chloro-phenyl)-6-fluoro-2-methyl-3H-quinazolin-4-one (1.04 g, 3.60 mmol) in tetrahydrofuran (7 mL) was added dropwise. The solution became intense red and was stirred 30 minutes. In a separate vessel a solution of 2-fluorobenzaldehyde (0.575 mL, 6.33 mmol) in tetrahydrofuran (20 mL) was prepared and chilled to −78 ° C. The cold red anion solution was added to the cold methyl 2-fluorobenzaldehyde solution via canula over 30 seconds. The resulting mixture was stirred 1 hour at −78° C. and then quenched with saturated aqueous bicarbonate and warmed to ambient temperature. The mixture was concentrated and the residue was diluted with water (50 mL), ethyl acetate (10 mL) and saturated aqueous sodium bisulfite (50 mL). This mixture was stirred 1 h and then repeatedly extracted with ethyl acetate. The combined extracts were washed with water and brine, dried over magnesium sulfate and concentrated. The residues from the two side by side reactions were combined and flash chromatographed on silica gel (45×150 mm) with elution proceeding as follows: 20% ethyl acetate/hexane (500 mL), nil; 30% ethyl acetate/hexane (500 mL) and 40% ethyl acetate/hexane (500 mL), two diastereomers of 3-(2-chloro-phenyl)-6-fluoro-2-[2-(2-fluoro-phenyl)-2-hydroxy-ethyl]-3H-quinazolin-4-one, both as viscous oils. The faster eluting diastereomer weighed 0.231 g (17%) and had: ¹H NMR δ7.92 (dd, J=3, 8.5 Hz, 1 H), 7.77 (dd, J=5, 9 Hz, 1 H), 7.60 (dd, J=1.5, 7.5 Hz, 1 H), 7.57-7.55 (m, 1 H), 7.53 (dd, J=3,8 Hz, 1 H), 7.48-7.42 (sym m, 2 H), 7.36-7.31 (m, 1 H), 7.24-7.18 (m,1 H), 7.12 (t, J=7.5 Hz, 1 H), 6.96-6.90 (m, 1 H), 5.65 (br s, 1 H), 5.55 (dd, J=2.5, 9 Hz, 1 H), 2.70 (dd, J=2.5, 17 Hz, 1 H), 2.61 (dd, J=9, 17 Hz, 1 H). The slower eluting diastereomer weighed 0.283 g (21%) and had: ¹H NMR δ7.91 (dd, J=3, 9 Hz, 1 H), 7.76 (dd, J=5, 9 Hz, 1 H), 7.58 (dd, J=1.5, 8 Hz, 1 H), 7.54 (dd, J=3, 9 Hz, 1 H), 7.51 (dd, J=1.5, 8 Hz, 1 H), 7.44 (dt, J=2, 8 Hz, 1 H), 7.39 (dt, J=1.5, 8 Hz, 1 H), 7.23-7.17 (m, 1 H), 7.13-7.07 (m, 2 H), 6.98-6.91 (m, 1 H), 5.61 (br s, 1 H), 5.57 (dd, J=4, 8 Hz, 1 H), 2.72-2.60 (m, 2 H).

Separation of Atropisomer by HPLC

The HPLC separation of the atropisomers of 2-{[3-(2-chloro-phenyl)-6-fluoro-4-oxo-3,4-dihydro-quinazolin-2-yl]-1-hydroxy-vinyl}-6-methyl-nicotinonitrile is described below.

| Column | Chiralpak AD |
|---|---|
| Mobile Phase | 70/30 hexane/isopropyl alcohol with 0.1% diethylamine |
| Flow Rate | 1 mL/min |
| Detection | UV (250 nM) |
| Retention Time (first atropisomer) | 16.678 min |
| Retention Time (second atropisomer) | 22.195 min |

What is claimed is:

1. A compound of the formula

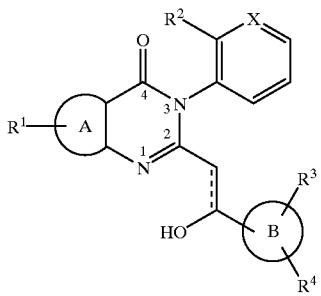

I wherein the dashed line represents an optional double bond;

A is a benzo or thieno fused aromatic ring;

B is phenyl, pyridyl or pyrimidyl;

X is N or CH;

$R^1$ is selected from hydrogen, $(C_1-C_6)$alkyl optionally substituted with from one to three fluorine atoms, cyano, halo, amino, nitro and $(C_1-C_6)$alkoxy optionally substituted with from one to three fluorine atoms;

$R^2$ is halo, cyano, $(C_1-C_6)$ alkyl optionally substituted with from one to three fluorine atoms, nitro, amino, $(C_1-C_6)$alkylthio, $(C_1-C_6)$alkoxy optionally substituted with from one to three fluorine atoms, hydroxy, H—C(=O)—, $(C_1-C_6)$alkyl—O—C(=O)— or $NH_2$—C(=O)—;

when X is N, $R^3$ and $R^4$ are selected, independently, from hydrogen, $(C_1-C_6)$alkyl optionally substituted with from one to three fluorine atoms, halo, cyano, hydroxy $(C_1-C_6)$alkoxy optionally substituted with from one to three fluorine atoms, —C(=O)H, —$CH_2OR^5$ and —$CH_2NR^6R^7$;

when X is CH, one of $R^3$ and $R^4$ is selected, from cyano, hydroxy $(C_1-C_6)$alkoxy optionally substituted with from one to three fluorine atoms, —C(=O)H, —$CH_2OR^5$ and —$CH_2NR^6R^7$ and the other of $R^3$ and $R^4$ is selected from hydrogen, $(C_1-C_6)$alkyl optionally substituted with from one to three fluorine atoms, halo, cyano, hydroxy $(C_1-C_6)$alkoxy optionally substituted with from one to three fluorine atoms, —C(=O)H, —$CH_2OR^5$ and —$CH_2NR^6R^7$;

$R^5$ is hydrogen, $(C_1-C_6)$alkyl or —C(=O)$(C_1-C_6)$alkyl; and $R^6$ and $R^7$ are selected, independently, from hydrogen, $(C_1-C_6)$alkyl and —C(=O)$(C_1-C_6)$alkyl;

or R⁶ and R⁷, taken together with the nitrogen to which they are attached, form a four to seven membered saturated or unsaturated ring wherein one of the carbon atoms of such ring may optionally be replaced by oxygen or nitrogen;

and the pharmaceutically acceptable salts of such compounds.

2. A compound according to claim 1 wherein ring A is benzo.

3. A compound according to claim 1 wherein ring B is phenyl or 2-pyridyl.

4. A compound according to claim 2 wherein R¹ is hydrogen or halo and R² is halo or (C₁–C₆)alkyl.

5. A compound according to claim 4 wherein R¹ is fluoro and R² is chloro or methyl.

6. A compound according to claim 1 wherein the bond represented by a solid and dashed line is a double carbon-carbon bond.

7. A compound according to claim 6 wherein ring A is benzo and ring B is phenyl or 2-pyridyl.

8. A compound according to claim 7 wherein R¹ is fluoro.

9. A compound according to claim 8 wherein R³ is cyano, hydrogen, fluoro or methyl.

10. A compound according to claim 8 wherein R² is chloro or methyl.

11. A compound according to claim 3 wherein R³ is cyano and R⁴ is methyl.

12. A compound according to claim 1 wherein said compound is selected from the group consisting of:

3-(2-chloro-phenyl)-6-fluoro-2-[2-hydroxy-2-(6-methyl-pyridin-2-yl)-vinyl]-3H-quinazolin-4-one;

2-{2-[3-(2-chloro-phenyl)-6-fluoro-4-oxo-3,4-dihydro-quinazolin-2-yl]-1-hydroxy-vinyl}-6-methyl-nicotinonitrile;

2-{2-[3-(2-chloro-phenyl)-6-fluoro-4-oxo-3,4-dihydro-quinazolin-2-yl]-1-hydroxy-vinyl}-nicotinonitrile;

2-{2-[3-(2-chloro-phenyl)-6-fluoro-4-oxo-3,4-dihydro-quinazolin-2-yl]-1-hydroxy-vinyl}-benzonitrile;

2-{2-[3-(2-chloro-pyridin-3-yl)-6-fluoro-4-oxo-3,4-dihydro-quinazolin-2-yl]-1-hydroxy-vinyl}-nicotinonitrile;

2-{2-[3-(2-chloro-pyridin-3-yl)-6-fluoro-4-oxo-3,4-dihydro-quinazolin-2-yl]-1-hydroxy-vinyl}-6-methyl-nicotinonitrile;

3-(2-chloro-phenyl)-6-fluoro-2-(2-hydroxy-2-pyridin-2-yl-vinyl)-3H-quinazolin-4-one;

2-{2-[6-fluoro-3-(2-methyl-pyridin-3-yl)-4-oxo-3,4-dihydro-quinazolin-2-yl]-1-hydroxy-vinyl}-benzonitrile;

2-{2-[3(2-chloro-pyridin-3-yl)-6-fluoro-4oxo-3,4-dihydro-quinazolin-2-yl]-1-hydroxy-vinyl}-benzonitrile; and 3-(2-chloro-phenyl)-6-fluoro-2-[2-(2-fluoro-phenyl)-2-hydroxy-ethyl]-3H-quinazolin-4-one.

13. A pharmaceutical composition for treating a condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising an amount of a compound according to claim 1 that is effective in treating such condition and a pharmaceutically acceptable carrier.

14. A pharmaceutical composition for treating a disorder or condition, the treatment of which can be effected or facilitated by reducing or inhibiting glutamate neurotransmission in a mammal, comprising an amount of a compound according to claim 1 that is effective in treating such disorder or condition and a pharmaceutically acceptable carrier.

15. A method for treating a condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal requiring such treatment an amount of a compound according to claim 1 that is effective in treating such condition.

16. A method for treating a disorder or condition, the treatment of which can be effected or facilitated by reducing or inhibiting glutamate neurotransmission in a mammal, comprising administering to a mammal requiring such treatment an amount of a compound according to claim 1 that is effective in treating such disorder or condition.

17. A pharmaceutical composition for treating a condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising an AMPA receptor antagonizing effective amount of a compound according to claim 1 and a pharmaceutically acceptable carrier.

18. A pharmaceutical composition for treating a disorder or condition, the treatment of which can be effected or facilitated by reducing or inhibiting glutamate neurotransmission in a mammal, comprising an AMPA receptor antagonizing effective amount of a compound according to claim 1 and a pharmaceutically acceptable carrier.

19. A method for treating a condition selected from stroke, cerebral ischemia, spinal cord trauma, head trauma, Alzheimer's Disease, Huntington's Chorea, amyotrophic lateral sclerosis, AIDS-induced dementia, muscular spasms, migraine headaches, urinary incontinence, psychosis, convulsions, perinatal hypoxia, cardiac arrest, hypoglycemic neuronal damage, opiate tolerance and withdrawal, ocular damage and retinopathy, idiopathic and drug induced Parkinson's Disease, anxiety, emesis, brain edema, chronic or acute pain, tardive dyskinesia and cerebral deficits subsequent to cardiac bypass surgery and grafting, in a mammal, comprising administering to a mammal requiring such treatment an AMPA receptor antagonizing effective amount of a compound according to claim 1.

20. A method for treating a disorder or condition, the treatment of which can be effected or facilitated by reducing or inhibiting glutamate neurotransmission in a mammal, comprising administering to a mammal requiring such treatment an AMPA receptor antagonizing effective amount of a compound according to claim 1.

* * * * *